United States Patent [19]

Olsen

[11] 4,273,131

[45] Jun. 16, 1981

[54] SURGICAL STYLET

[75] Inventor: C. Eric Olsen, Oxnard, Calif.

[73] Assignee: Auburn Enterprises, Inc., Ventura, Calif.

[21] Appl. No.: 49,949

[22] Filed: Jun. 18, 1979

[51] Int. Cl.³ .................................. A61M 29/00
[52] U.S. Cl. ........................................... 128/341
[58] Field of Search ............. 128/341, 303 R, 303.11, 128/303.12

[56] References Cited

U.S. PATENT DOCUMENTS

| 702,789 | 6/1902 | Gibson | 128/341 |
|---|---|---|---|
| 1,957,673 | 5/1934 | Sayre | 128/341 |
| 2,756,752 | 7/1956 | Scherlis | 128/303 R |
| 3,185,155 | 5/1965 | Slaten et al. | 128/303 R |
| 3,508,553 | 4/1970 | Kanbar et al. | 128/303 R |
| 3,613,664 | 10/1971 | Willson et al. | 128/303 R |
| 3,630,190 | 12/1971 | Baker | 128/341 |
| 3,741,214 | 6/1973 | Tillander | 128/341 |
| 3,788,325 | 1/1974 | Jacobsen | 128/303 R |
| 3,805,767 | 4/1974 | Erb | 128/303 R |
| 3,999,551 | 12/1976 | Spitz et al. | 128/303 R |

FOREIGN PATENT DOCUMENTS 94381 10/1897 Fed. Rep. of Germany .......... 128/341
1196437 5/1959 France ................................. 128/341

Primary Examiner—John D. Yasko
Attorney, Agent, or Firm—Jack C. Munro

[57] ABSTRACT

The surgical stylet formed as an elongated, thin member which includes a metallic core which is capable of being bent and remain stationary in any particular desired configuration. A rigid plastic is extruded over the core with the fore end of the core being exposed. The fore end of the core includes an enlarged section. The outermost tip of the fore end is smoothly contoured. A second exterior covering is located about the fore end and extends a short distance beyond the tip. The second exterior covering is formed of a plastic substantially softer than the first covering. The second exterior covering is secured to the fore end with the enlarged section of the fore end to facilitate this securement. The thickness of both the first and second exterior coverings may be such so as to permit the including of longitudinal passageways through the coverings. Within each passageway there is to be located a thin wire member which is capable of being manually moved within the passageway. The forward end of the thin wire member is to be specially configured such as in the shape of a hook.

5 Claims, 6 Drawing Figures

U.S. Patent  Jun. 16, 1981  4,273,131
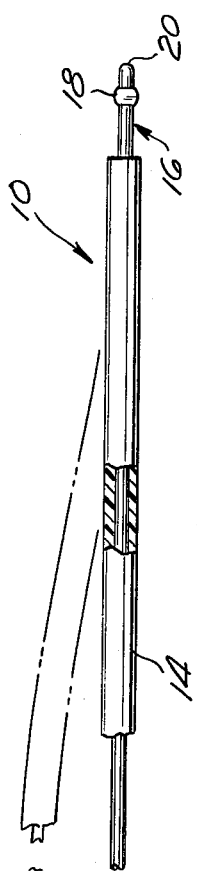
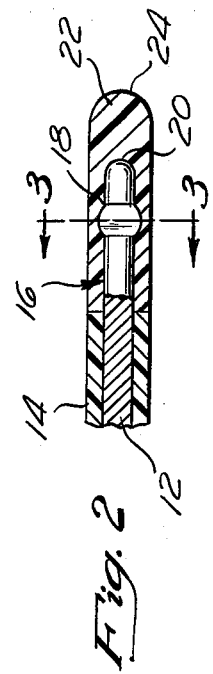
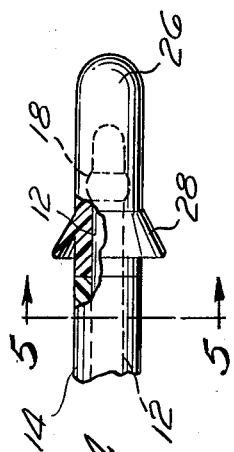
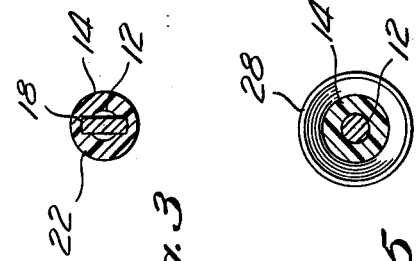
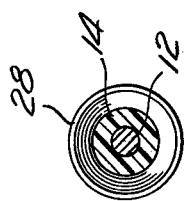
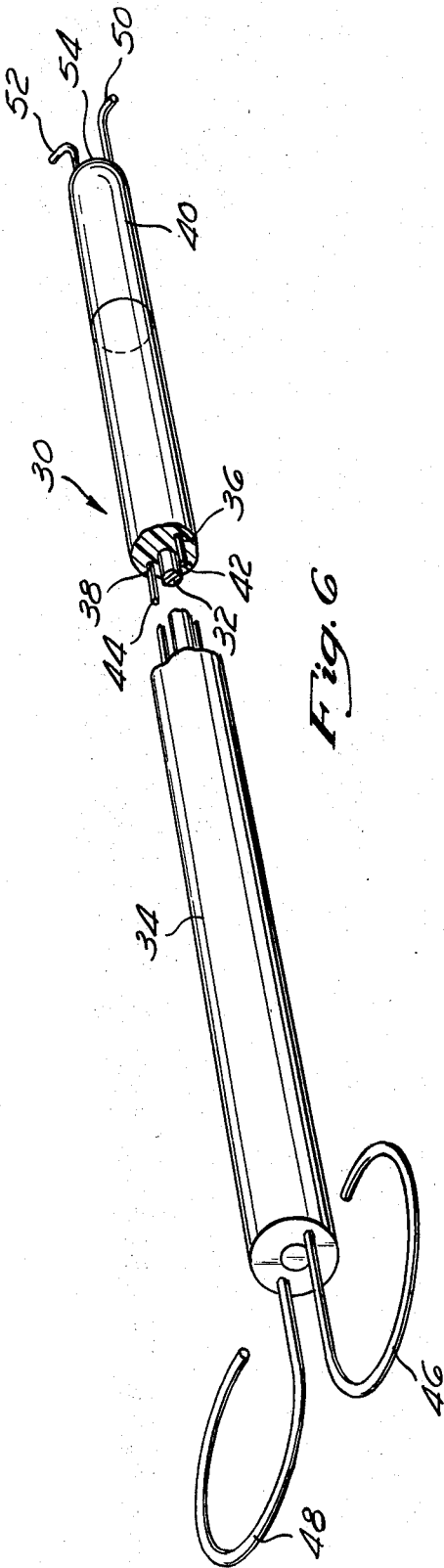

SURGICAL STYLET

BACKGROUND OF THE INVENTION

The field of this invention relates of medical products and more particularly to a probing device which is to be referred to as a surgical stylet. Said stylet is to be used to be inserted within cavities of a human body such as into veins and body cavity openings.

It has been known in the past to employ the use of a surgical stylet by a physician when examining a patient. Such a stylet can be used to initiate entry into a body cavity, such as through the cervix, or even into the uterus. Also, stylets have been employed into veins and arteries for the purpose of opening a blocked or partially blocked vein or artery.

In the past, such surgical stylets were formed of a bendable metallic core which was entirely covered with a rigid plastic material. It is desirable to have the main body portion of the stylet covered with a rigid plastic so as to facilitate grasping and precise maneuverability of the stylet. However, the forward tip of the stylet is therefore inherently sharp and the use of such a sharp tip is undesirable. It is not at all uncommon that, during the use of the stylet, the tip portion is caused to accidentally puncture or penetrate a section of tissue which it was not desirable to puncture or penetrate.

Additionally, previous stylets could only be employed as merely a probing device. it has not been known in the past to incorporate any other structure in conjunction with the stylet which could facilitate the obtaining of tissue specimens or could be used to perform other operations such as removing deposits from the inside surface of a vein or artery.

SUMMARY OF THE INVENTION

The structure of this invention is believed to be summarily described in the Abstract of the Disclosure and reference is to be had thereto.

The primary objective of this invention is to construct a surgical stylet which has a soft resilient forward tip which substantially decreases the chances of the tip of the stylet from accidentally penetrating or puncturing sections of tissue.

Another objective of this invention is to expand the use of a surgical stylet by incorporating therein certain features and/or instruments to facilitate removal of tissue specimens or foreign deposits within the body.

BRIEF DESCRIPTION OF THE DRAWING

FIG. 1 is a longitudinal elevational view of a first embodiment of the surgical stylet of this invention showing the stylet prior to attachment of the soft plastic tip portion;

FIG. 2 is a cross-sectional view of the tip portion of the stylet of FIG. 1 showing the attachment of the soft plastic portion;

FIG. 3 is a cross-sectional view taken along line 3—3 of FIG. 2;

FIG. 4 is a view similar to FIG. 2 but of a modified form of fore end portion of the stylet;

FIG. 5 is a cross-sectional view taken along line 5—5 of FIG. 4; and

FIG. 6 is a longitudinal isometric view, partially broken away, of a second embodiment of surgical stylet of this invention incorporating not only the constructional features of the first embodiment, but adding movable wire members within the body portion of the stylet.

DETAILED DESCRIPTION OF THE SHOWN EMBODIMENT

Referring particularly to the drawing, there is shown in FIG. 1 a first embodiment 10 of a surgical stylet of this invention which takes the form generally of a bendable metallic core 12 and a first exterior covering 14. The core 12 is to comprise a section of metallic wire usually of steel or aluminium or alloys thereof. The diameter of the core 12 will normally be in the range of 1/32 of an inch to 1/16 of an inch. It is to be understood that the core 12 can be manually bent and will remain in that bent configuration until it is desired to again rebend the core 12. This bending of the core 12 is normally desirable to configure the stylet 10 into a specific configuration for use in that specific configuration.

The material of construction of the covering 14 is to comprise a plastic material such as a polyethylene plastic. The plastic coating 14 is to be sufficiently rigid so as to permit secure grasping of the stylet 10 and precise manipulation or maneuvering of the stylet. Also, the stylet 10 of this invention is intended to be used only once and is to then be disposed of. This is preferred in order to diminish the chance of spreading infection or disease. In order to insure that the stylet 10 will be used only once, the plastic covering 14 will melt and therefore prevent reuse of the stylet.

The fore end 16 of the stylet 10 includes an enlarged section 18. Enlarged section 18 is merely a crimped section. But it is to be understood that other types of enlarged sections could be employed such as an annular enlarged section. Also, it is to be noted that in order to prevent the possibility of accidental tissue damage, the outermost tip 20 of the stylet is smoothly contoured as being rounded.

Secured about the fore end 16 is a second plastic covering 22. The plastic covering 22 is to be substantially softer than the covering 14. Actually, the covering 22 can be readily compressed. Also, it is to be noted that there is a substantial amount of the covering 22 located between the outermost tip 24 of the covering 22 and the tip 20. This softness of the covering 22 is to diminish the chance of accidentally puncturing tissue, such as an organ.

It is very undesirable to have the covering 22 become accidentally dislodged from the fore end 16, since the covering may become lodged in a body cavity. The covering 22 will be adhesively secured to the fore end 16 and also adhesively secured to the covering 14. It is to be noted that the cross-sectional configuration of the covering 22 is identical to the cross-sectional configuration of the covering 14. The enlarged section 18 of the fore end 16 is to further facilitate securing of the covering 22 to the fore end 16.

Referring particularly to FIGS. 4 and 5, there is shown a modified form of second exterior covering 26 which includes a conical flange 28. The material of construction of the covering 26 will be identical to that of covering 22. The conical flange 28 is to be pushed against the exterior surface of the covering 26 during insertion of the stylet. However, upon withdrawing movement of the stylet, the conical flange 28 will function to expand outwardly and tend to remove desposited material such as desposits on the inside of a vein or artery.

Referring particularly to FIG. 6 of the drawing, there is shown a second embodiment of stylet 30. The stylet 30 is to include a core 32 basically identical to core 12. Extruded onto the core 32 is a first exterior covering 34 which is basically similar in construction to the exterior covering 14. The only difference with the covering 34 is that it is formed to be somewhat thicker so as to permit the location of a pair of longitudinal passageways 36 and 38 therein. Each of the passageways 36 and 38 are parallel to the longitudinal center axis of the core 32 and extend entirely through the first exterior covering 34 and through the tip portion 40. It may be desirable to employ only one passageway or more than the two passageways. The tip portion 40 is basically identical to the tip portion 22.

Located within the passageway 36 is a thin rigid wire member 42. A similar wire member 44 is located within the passageway 38. The wire member 42 is movable within the passageway 38 by manual operation of handle section 46. A similar handle section 48 is to be employed for manually moving a wire member 44. The anticipated diametrical size of the wire members 42 and 44 will be approximately 5/1,000 of an inch.

The forward end of the wire member 42 is formed into a hooked section 50. A similar hooked section 52 is formed at the forward end of the wire member 44. The hooked sections 50 and 52 can be brought snugly against the outermost tip section 54 of the second exterior covering 40. This would be the initial position of the members 42 and 44 during insertion of stylet 30 such as through a vein or through a body cavity. Once the stylet 30 has reached the desired location, the physician or operator of the stylet 30, can then manually longitudinally cause the wire members 42 and 44 to move so that the hooked sections 50 and 52 extend forwardly of the outermost tip 54. The hooked sections 50 and 52 can be manipulated to grasp onto a section of tissue such as a blood clot or other type of tissue.

It is to be understood that it is considered to be within the scope of this invention that the sections 50 and 52 can take other configurations other than the hooked sections shown.

What is claimed is:

1. A surgical stylet comprising:
   an elongated member formed of a core and a first exterior covering, said core being of a solid metal but bendable into a variety of different configurations, said core having a longitudinal center axis, said first exterior covering comprising a rigid plastic;
   said elongated member having a fore end and an aft end, said core extending into said fore end, said core having a tip, said tip being smoothly contoured, a second exterior covering extending beyond said tip, said second exterior covering being formed of a resilient cushiony plastic so as to deter the making of puncture wounds in tissue during use of the stylet; and
   said first exterior covering being extruded upon said core, said core being of uniform cross-sectional configuration, said exterior covering being of uniform cross-sectional configuration.

2. The surgical stylet as defined in claim 1 wherein:
   said second exterior covering having a cross-sectional configuration identical to said first exterior covering.

3. The surgical stylet as defined in claim 2 wherein:
   said fore end including a widened section, whereby said widened section is to function to securely retain said second exterior coating and prevent accidental dislodgement of such during use of the stylet.

4. The surgical stylet as defined in claim 3 wherein:
   a longitudinal passageway formed through the entire length of said first exterior covering and said second exterior covering, said passageway being located substantially parallel to said longitudinal center axis of said core, a rigid wire member being located within said passageway, said rigid wire member extending exteriorly of said passageway, said rigid wire member being manually movable within said passageway, whereby a portion of said wire member is to extend exteriorly of said second exterior covering and is to be capable of performing a function such as latching onto a piece of tissue or the like.

5. A surgical stylet comprising:
   an elongated member formed of a core and a first exterior covering, said first exterior covering closely conforming to the exterior surface of said core, said core being of a solid metal but bendable into a variety of different configurations, said core having a longitudinal center axis, said first exterior covering comprising a rigid material;
   said elongated member having a fore end and an aft end, said core extending into said fore end, said core having a tip, said tip being smoothly contoured, a second exterior covering extending beyond said tip, said second exterior covering being formed of a resilient cushiony material so as to deter the making of puncture wounds in tissue during use of the stylet; and
   a longitudinal passageway formed through said entire length of said first exterior covering and said second exterior covering, said passageway being located substantially parallel to and spaced from said longitudinal center axis of said core, a rigid wire member being located within said passageway, said rigid wire member extending exteriorly of said passageway, said rigid wire member being manually movable within said passageway, a portion of said wire member extends exteriorly of said second exterior covering and is capable of performing a function such as latching onto a piece of tissue or the like.

* * * * *